(12) United States Patent
Gwon et al.

(10) Patent No.: US 11,185,553 B2
(45) Date of Patent: Nov. 30, 2021

(54) PHARMACEUTICAL COMPOSITION FOR PREVENTING OR TREATING ISCHEMIC-REPERFUSION INJURY COMPRISING BILE ACIDS

(71) Applicant: SAMSUNG LIFE PUBLIC WELFARE FOUNDATION, Seoul (KR)

(72) Inventors: Hyeon Cheol Gwon, Seoul (KR); Hyung Suk Jang, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 188 days.

(21) Appl. No.: 16/345,483

(22) PCT Filed: Oct. 31, 2017

(86) PCT No.: PCT/KR2017/012127
§ 371 (c)(1),
(2) Date: Apr. 26, 2019

(87) PCT Pub. No.: WO2018/080276
PCT Pub. Date: May 3, 2018

(65) Prior Publication Data
US 2019/0247406 A1    Aug. 15, 2019

(30) Foreign Application Priority Data
Oct. 31, 2016 (KR) .................. 10-2016-0143393

(51) Int. Cl.
*A61K 31/575* (2006.01)
*A61P 9/10* (2006.01)
*A23L 33/10* (2016.01)
*A23L 29/00* (2016.01)

(52) U.S. Cl.
CPC .......... *A61K 31/575* (2013.01); *A23L 29/035* (2016.08); *A23L 33/10* (2016.08); *A61P 9/10* (2018.01); *A23V 2200/326* (2013.01); *A23V 2250/03* (2013.01)

(58) Field of Classification Search
CPC ........ A61K 31/575; A61L 29/035; A61P 9/10
USPC ......................................................... 514/182
See application file for complete search history.

(56) References Cited

FOREIGN PATENT DOCUMENTS

| CN | 1853639 | 11/2006 |
|---|---|---|
| KR | 10-2000-0065178 | 11/2000 |
| KR | 10-1414810 | 7/2014 |

OTHER PUBLICATIONS

Chen et al., Naunyn-Schmiedeberg's Arch Pharmacol, 2012, 365, 797-806 (Year: 2012).*
Lee, W.Y. et al., "Effect of ursodeoxycholic acid on ischemia/reperfusion injury in isolated rat heart", Archives of Pharmacal Research, 1999, vol. 22(5), pp. 479-484.
Akdemir, A. et al., "Is ursodeoxycholic acid crucial for ischemia/reperfusion-induced ovarian injury in rat ovary?", Archives of Gynecology and Obstetrics, 2015, vol. 292(2), pp. 445-450. (Abstract only).
International Search Report and Written Opinion of the International Searching authority of International Application No. PCT/KR2017/012127 dated Jan. 30, 2018.

* cited by examiner

*Primary Examiner* — Yevgeny Valenrod
(74) *Attorney, Agent, or Firm* — Ping Wang; Morris, Manning & Martin LLP (57) ABSTRACT

The present invention relates to a composition for preventing, treating, or alleviating ischemia-reperfusion injury, containing bile acid. According to the present invention, bile acid increases intranuclear beta-catenin levels, interferes with the opening of a mitochondria permeable transition pore (mPTP), and has excellent effects, in ischemia-reperfusion injury animal models, of alleviating tissue injury and reducing the size of infarcts, thereby being usable in the prevention, treatment, or alleviation of ischemia-reperfusion injury.

5 Claims, 4 Drawing Sheets

PHARMACEUTICAL COMPOSITION FOR PREVENTING OR TREATING ISCHEMIC-REPERFUSION INJURY COMPRISING BILE ACIDS

TECHNICAL FIELD

The present invention relates to a composition for the prevention, treatment or amelioration of an ischemia-reperfusion injury, the composition containing bile acid or a pharmaceutically acceptable salt thereof.

BACKGROUND ART

Blood delivers oxygen and nutrients to the respective tissues and cells of the body. Ischemia refers to a state of oxygen deficiency in which the blood vessels, which are used to supply blood to body organs, tissues, or parts, narrow or shrink, or normal blood vessels are not sufficiently produced, resulting in lack of blood supply. Ischemia irreversibly injures cells and leads to tissue necrosis. In particular, the brain or heart is the most sensitive body organ to the lack of blood supply. For example, when ischemia occurs in a tissue due to stroke or head injury, a series of processes called ischemic cascades are triggered so that the tissue is permanently injured. To prevent such tissue injury, the flow of blood again after ischemia is called reperfusion.

Conventional therapy for ischemia and consequent hypoxia is to restore blood flow and oxygen delivery to normal levels either by increasing the systemic oxygen supply or by eliminating the cause of vascular occlusion. However, there is a problem that restoration of blood flow and oxygen delivery results in additional cell death or loss of function, irrespective of the injury caused by ischemia or hypoxia. Additional injury caused by restoration of blood flow and oxygen delivery is known as reperfusion injury. Tissue injury caused by reperfusion injury appears to be similar to acute inflammatory conditions resulting from adherence of inflammatory cells to reperfused tissue to cause the activation of these inflammatory cells and subsequent formation of free radicals. Generation of free radicals and other cytotoxic biomolecules in reperfused tissue may lead to cell death by necrosis or activation of apoptotic pathways.

Meanwhile, mitochondrial permeability transition pore (mPTP) is formed in the mitochondrial inner membrane, and when mPTP is opened, molecules below 1500 Da may enter into the mitochondrial membrane. The result of mPTP opening is swelling of the outer mitochondrial membrane and ultimate bursting as well as uncoupling of oxidative phosphorylation, the subsequent release of stored calcium and pre-apoptotic factors. The release of stored calcium may cause mitochondrial permeability transition (MPT) in neighboring mitochondria resulting in the production of calcium-overload, reactive oxygen species (ROS) production and cell-mediated chain reaction. Subsequently, depending on the energy state of the cells, apoptosis or necrosis occurs to cause irreversible tissue and organ injury.

The roles of mitochondria-mediated apoptosis and necrosis in the pathogenesis of many diseases are well established. It is known that mPTP is responsible for the pathogenesis and progression of several diseases such as acute myocardial infarction, stroke, neurological diseases and hepatitis.

In particular, myocardial infarction is caused by myocardial cell death resulting from necrosis and/or apoptosis due to sequential ischemic reperfusion in ischemic heart disease. Fatal reperfusion injury (myocardial cell death as a direct consequence of tissue reperfusion) is believed to account for up to 50% of the final myocardial infarction size and is known to be dependent on reperfusion injury salvage kinase (RISK) pathway and mPTP opening.

There has been no report on the association of bile acids and mPTP with these functions. As described above, effective treatment for ischemia-reperfusion injury, an important disease with a high incidence, is insufficient. Thus, the effective prevention and treatment of ischemia-reperfusion injury using bile acids would have significant ripple effects.

DISCLOSURE

Technical Problem

Accordingly, the inventors of the present invention confirmed that deoxycholic acid, cholic acid, and lithocholic acid in bile acids could inhibit ischemia-reperfusion injury while studying the relationship between mPTP and bile acids, thereby completing the present invention.

Therefore, an object of the present invention is to provide a pharmaceutical composition for preventing or treating ischemia-reperfusion injury containing bile acids or a pharmaceutically acceptable salt thereof and a food composition for preventing or ameliorating ischemia-reperfusion injury.

Technical Solution

In order to achieve the above-identified objects, the present invention provides a pharmaceutical composition for preventing or treating ischemia-reperfusion injury containing bile acids or a pharmaceutically acceptable salt thereof.

Further, the present invention provides a food composition for preventing or ameliorating ischemia-reperfusion injury, the composition containing bile acids or a pharmaceutically acceptable salt thereof.

Advantageous Effects

According to the present invention, bile acids increase intranuclear beta-catenin (β-catenin) levels, interferes with the opening of a mitochondrial permeability transition pore (mPTP), and has excellent effects, in ischemia-reperfusion injury animal models, of alleviating tissue injury and reducing the size of infarcts, thereby being usable in the prevention, treatment, or alleviation of ischemia-reperfusion injury.

MODES OF THE INVENTION

Hereinafter, the present invention is described in detail.

The present invention provides a pharmaceutical composition for preventing or treating ischemia-reperfusion injury, the composition containing a bile acid or a pharmaceutically acceptable salt thereof.

In the present invention, bile acids have excellent effects of increasing intranuclear beta-catenin levels, interfering with the opening of a mitochondria permeability transition pore (mPTP), and alleviating tissue injury and reducing the size of infarcts in ischemia-reperfusion injury animal models, thereby being usable in the prevention, treatment, or alleviation of ischemia-reperfusion injury.

In the present invention, bile acids may be at least one selected from the group consisting of ursodeoxycholic acid, glycochenodeoxycholic acid (GlycochenDCA), taurodeoxycholic acid (TauroDCA), glycocholic acid, taurocholic acid (TauroCA), chenodeoxycholic acid (ChenoDCA), cholic acid, dehydrocholic acid, lithocholic acid and deoxycholic acid (DCA), preferably cholic acid, lithocholic acid or deoxycholic acid, but is not limited thereto.

The cholic acid, lithocholic acid and deoxycholic acid of the present invention can effectively prevent and treat ischemia-reperfusion injury even at a low concentration.

Unless specified otherwise, the pharmaceutically acceptable salt of bile acids of the present invention includes an acidic or basic salt which may be present in the bile acids. For example, the pharmaceutically acceptable salt includes sodium, calcium and potassium salts having a hydroxyl group. Further, hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts having an amino group. The pharmaceutically acceptable salt may be prepared by the methods well known in the art. The pharmaceutically acceptable salt preferably is sodium gluconate salt or sodium taurate salt, but is not limited thereto.

In the present invention, "ischemic injury" refers to injury occurring as a result of a restriction in blood supply and hence the shortage of oxygen supply to organs requiring blood supply such as the heart, brain, kidneys, etc., which can lead to fatal damage such as dysfunction of tissues and cell death. The cause of an ischemic injury includes vascular disease, coronary thrombosis, cerebrovascular thrombosis, aneurysm rupture, systemic hemorrhage, crush injury, sepsis, severe skin burn, vascular ligation surgery (e.g., spinal ischemia during thoracoabdominal aneurysm surgery), cardiopulmonary bypass, organ transplantation, cardiopulmonary collapse (sudden cardiac death), suffocation, etc., but is not limited thereto.

In the present invention, the "ischemic injury" also includes ischemic-reperfusion injury that may occur, for example, during organ transplantation, in addition to ischemic injury conventionally caused.

In the present invention, "ischemia-reperfusion injury" may be caused by at least one selected from the group consisting of myocardial ischemia, cerebrovascular ischemia, renal ischemia, liver ischemia, ischemia reperfusion myocarditis, skin ischemia, enteral ischemia, intestinal ischemia, gastric ischemia, pulmonary ischemia, pancreatic ischemia, skeletal muscular ischemia, abdominal muscular ischemia, limb ischemia, ischemia reperfusion colitis, mesenteric ischemia and symptomless ischemia, but is not limited thereto.

The ischemia-reperfusion injury may be caused by restoration of blood flow in a tissue or organ that has undergone a natural event such as restoration of blood flow after trauma (e.g., acute myocardial infarction) or blood supply reduction; or reperfusion surgery (e.g., one or more surgical procedures to restore blood flow in a tissue or organ that has undergone blood supply reduction), other therapeutic interventions, or organ transplant procedures. Such surgical procedures include, for example, coronary artery bypass surgery, coronary angioplasty, organ transplant procedure and the like.

For example, acute myocardial infarction refers to the phenomenon of death and necrosis of the heart muscle due to lack of oxygen and nutrients caused by the occlusion of one of the cardiac vessels. In this case, usually, the patient should visit the hospital, and the blood vessel should be reperfused within 1 hour. Therefore, the mortality rate can be reduced to within 10%. However, in about 10% of patients, myocardial cells are injured due to the rapid supply of oxygen resulting from reperfusion of blocked blood vessels, which is called reperfusion injury. Because of reperfusion injury, about 10% of the patients die within 30 days after the procedure, and about 30% of surviving patients have symptoms such as heart failure.

As used herein, the term "reperfusion surgery" refers to surgery or procedure for removing thrombus generated in blood vessels and allowing blood flow to flow again, which may include surgical thrombectomy and reperfusion-induced manipulation using a stent, but is not limited thereto. Reperfusion surgery can be used to complement the disadvantages of reperfusion therapeutic agent (e.g., plasminogen activators such as tPA).

The reperfusion surgery may include a method of suctioning thrombus by applying negative pressure (proximal thrombectomy), a method of removing thrombus with coil (distal thrombectomy), a method of inserting a stent into narrowed blood vessels to widen the blood vessels and removing thrombus with the stent together (stent retriever) and the like. The proximal thrombectomy is a method of removing thrombus by applying a negative pressure approaching the proximal thrombus, mainly using a suction device, such as the Penumbra system. The distal thrombectomy is a method of removing thrombus from a distal portion over thrombus with a wire, mainly using a coil device, such as the Merci system. The stent retriever is a method of inducing reperfusion of a blood vessel by inserting a stent like a coronary artery. The composition according to the present invention may be applied to various reperfusion surgeries for reperfusion purposes in addition to the above-mentioned surgeries.

In the present invention, the reperfusion surgery refers to surgery or treatment performed to treat cerebrovascular diseases, arteriosclerosis, cardiovascular diseases and the like, but is not limited thereto.

The cerebrovascular disease includes stroke, cerebral infarction, cerebral thrombosis and cerebral embolism, but is not limited thereto. The cardiovascular disease includes myocardial infarction and angina pectoris, but is not limited thereto.

The pharmaceutical composition of the present invention can be administered before, during, or after the occurrence of ischemia-reperfusion injury, for example, for pretreatment of reperfusion surgery. The pharmaceutical composition of the present invention is administered into the blood vessels of a patient prior to vascular reperfusion surgery so that it is useful for preventing, treating or ameliorating tissue injury, such as myocardial injury, after reperfusion.

Also, as described herein, lesions caused by ischemia and injury caused by ischemia or ischemic reperfusion can induce apoptosis in diseased cells, tissues or organs, leading to impairment and dysfunction. The present invention provides a method of preventing or treating an ischemia-reperfusion injury including contacting a bile acid or a pharmaceutically acceptable salt thereof with a cell, tissue or organ in need thereof, or administering a bile acid or a pharmaceutically acceptable salt thereof to a subject in need thereof. For the prevention or treatment of ischemic injury or ischemia-reperfusion injury, for example, the bile acid or pharmaceutically acceptable salt thereof of the present invention may be administered to a subject to undergo reperfusion surgery, for example, about 5 minutes, about 10 minutes, about 15 minutes, about 20 minutes, about 30 minutes, about 45 minutes, about 1 hour, about 2 hours, about 3 hours, about 4 hours, about 5 hours, about 12 hours, about 24 hours, or about 48 hours, and preferably about 2 hours before the reperfusion surgery.

Alternatively or additionally, the bile acid or pharmaceutically acceptable salt thereof of the present invention may be administered to a subject after reperfusion surgery or during reperfusion surgery. For example, the bile acid or pharmaceutically acceptable salt thereof may be administered more than once at regular intervals during the reperfusion surgery. Alternatively, the bile acid may be administered continuously over the duration of the reperfusion surgery. Also, for example, the bile acid of the present invention may be administered to a subject who underwent reperfusion surgery after reperfusion surgery. The bile acid of the present invention may be administered to a subject who underwent reperfusion surgery, for example, about 5 minutes, about 10 minutes, about 15 minutes, about 20 minutes, about 30 minutes, about 45 minutes, about 1 hour, about 2 hours, about 3 hours, about 4 hours, about 5 hours, about 12 hours, about 24 hours, or about 48 hours after the reperfusion surgery. The bile acid or acceptable salt thereof of the present invention may also be used to inhibit ischemia or ischemia-reperfusion injury to in vitro cells, tissues or organs (e.g., tissues used in transplantation procedures, organs used in organ transplantation) prior to reperfusion surgery. For example, the organ can be contacted with bile acid (e.g., immersing the organ in the bath with the composition containing bile acid of the present invention) prior to implanting the organ into the host body (e.g., during storage or transportation of the organ in a sterile environment) so as to inhibit ischemia or ischemia-reperfusion injury. Preferably, a single intravenous injection prior to reperfusion surgery of a subject having acute myocardial infarction can inhibit cardiac injury due to reperfusion surgery.

The pharmaceutical composition of the present invention may further include a therapeutic agent for reperfusion (therapeutic agent for recanalization). In addition, the pharmaceutical composition of the present invention can be used in combination with a reperfusion therapeutic agent.

The bile acid or pharmaceutically acceptable salt thereof of the present invention is an inhibitor of mPTP opening.

The bile acid or pharmaceutically acceptable salt thereof of the present invention is an agonist of beta-catenin.

The bile acid or pharmaceutically acceptable salt thereof of the present invention is for protecting mitochondrial.

The bile acid or pharmaceutically acceptable salt thereof of the present invention inhibits the infarction of the tissue.

The bile acid or pharmaceutically acceptable salt thereof of the present invention is an agonist of beta-catenin, which significantly reduces the phenomenon of death or necrosis of cardiac muscle caused by the opening of the mitochondrial permeability transition pore (mPTP) due to rapid oxygen uptake during reperfusion of the blocked blood vessels. Therefore, it can reduce the mortality rate of 10% within 30 days after reperfusion surgery and reduce the symptom of heart failure by about 30% of patients after reperfusion surgery. mPTP is formed in the mitochondrial inner membrane. mPTP is opened to induce depolarization of mitochondria, resulting in dysfunction of mitochondria. The bile acid acts as an agonist of beta-catenin, interfering the opening of mPTP to inhibit mitochondrial depolarization, thereby protecting mitochondria and preventing oxidative injury of mitochondria so as to inhibit tissue infarction. Accordingly, it has the effect of preventing, treating or ameliorating ischemia-reperfusion injury.

The pharmaceutical composition containing the bile acid or pharmaceutically acceptable salt thereof of the present invention may be formulated in the form of injectable or oral preparations. Further, the injectable preparation containing the pharmaceutical composition of the present invention may be administered through various routes including oral, transdermal, subcutaneous, intravenous, or muscular, but may preferably be administered intravenously. The injectable preparation containing the pharmaceutical composition of the present invention may be formulated using methods known in the art so as to provide a rapid, sustained or delayed release of the active ingredient after administration to the subject. The injectable preparation is preferably administered subcutaneously, muscularly or intravenously, and most preferably intravenously. When administered intravenously, it can be administered by intravenous injection once before reperfusion surgery, and the only one intravenous injection can effectively improve the injury of organs such as heart due to reperfusion surgery. Further, the oral preparation may be selected from the group consisting of tablets, pills, powders, granules, capsules, suspensions, solutions, emulsions, syrups and freeze-dried preparations, but is not limited thereto.

The bile acid or pharmaceutically acceptable salt thereof of the present invention may be administered to a subject via intraperitoneal administration, intranasal administration, intravenous injection, subcutaneous injection, intracerebrospinal injection, inhalation administration or oral administration. Further, the effective ingredients of the pharmaceutical composition of the present invention vary depending on the age, sex, weight, pathological condition and severity of the subject to be administered, route of administration, or judgment of the prescriber. Determination of the optimal dose based on these factors is within the level of those skilled in the art, but may be used at a similar or lower concentration relative to that of the FDA-approved concentration. More specifically, the daily dosage thereof is, for example, 0.1 mg/kg/day to 10 mg/kg/day, specifically 0.5 mg/kg/day to 5 mg/kg/day, more specifically 0.8 mg/kg/day to 3 mg/kg/day, furthermore specifically 1 mg/kg/day to 2 mg/kg/day, but is not limited thereto. The pharmaceutical composition of the present invention may be administered once to three times a day, but is not limited thereto.

Formulations for parenteral administration of the pharmaceutical compositions of the present invention can be injections, drops, lotions, ointments, gels, creams, suspensions, emulsions, suppositories, patches or spray agents, but are not limited thereto. Further, the pharmaceutical composition of the present invention may contain additives such as diluents, excipients, lubricants, binders, disintegrants, buffers, dispersants, surfactants, colorants, fragrances or sweeteners as necessary. The pharmaceutical composition of the present invention can be prepared by a conventional method in the art.

The pharmaceutical composition of the present invention may be administered alone or in combination with one or more other therapeutic agents, before, after, or concurrently with other therapeutic agents. The bile acid of the present invention and other therapeutic agents as described above may be co-administered simultaneously (e.g., co-administration) as a separate formulation or as a co-formulation. Alternatively, the agonist can be administered sequentially as a separated composition within a reasonable time frame as determined by a skilled clinician (e.g., for a time sufficient to allow overlapping of the pharmacological effects of the therapeutic agents by the therapy). The bile acid and one or more other therapeutic agents of the present invention may be administered in a single dose or in multiple doses according to such schedules in an order suitable for achieving the desired therapeutic effect (e.g., reduction and/or inhibition of ischemia, reduction and/or inhibition of ischemic injury; and reduction and/or inhibition of ischemia-reperfusion injury). Suitable dosages and administration therapy can be determined by the clinician and depend on the selected agonist(s), pharmaceutical formulation and route of administration, various patient factors, and other considerations.

Other suitable therapeutic agents that may be administered with the pharmaceutical composition of the present invention include calcium channel blockers, beta blockers, nitroglycerin, aspirin, anti-inflammatories, sodium diuretics, vasodilators, thrombolytic agents and antithrombotic agents, but are not limited thereto.

Further, the present invention provides a food composition for preventing or ameliorating ischemia-reperfusion injury, the composition containing a bile acid or pharmaceutically acceptable salt thereof.

The food composition can be used for health food, and in the present invention, the bile acid can be added intact or used with other food or food ingredients in the health food and can be suitably used according to conventional methods. There is no particular limitation on the kind of food. Examples of the food include drinks, meat, sausage, bread, biscuits, rice cakes, chocolates, candies, snacks, confectionery, pizza, ramen noodles, other noodles, gums, dairy products including ice cream, various soups, beverage, alcohols, and vitamin complexes, and it includes all healthy foods in a conventional sense.

The bile acid or pharmaceutically acceptable salt thereof of the present invention may be added intact to the food or can be used together with other food or food ingredients and may be suitably used according to conventional methods. The amount of the active ingredient to be mixed may be suitably determined according to its use purpose (for prevention or amelioration). Generally, the amount of bile acid in the health food may be added in an amount of 0.01% by weight to 15% by weight of the total weight of the food, and the amount of bile acid in the health beverage composition may be added in an amount of 0.02 g to 5 g, preferably 0.3 g to 1 g with respect to 100 ml of the health beverage composition. However, the amount may be less than the above-described range in the case of long-term intake intended for health and hygiene purposes or for health control purposes. Since there is no problem in terms of safety, the active ingredient can be used in an amount exceeding the above-described range.

The health functional beverage composition of the present invention has no particular limitation on other components other than those containing bile acid as an active ingredient in the indicated ratio and may contain various flavors or natural carbohydrates as an additional ingredient as conventional beverages. Examples of the above-mentioned natural carbohydrates include monosaccharides such as glucose and fructose; disaccharides such as maltose and sucrose; and polysaccharides such as conventional sugars including dextrin and cyclodextrin and sugar alcohols including xylitol, sorbitol, erythritol, and the like. Natural flavors such as tau martin and *stevia* extracts (e.g., rebaudioside A, glycyrrhizin, etc.) and synthetic flavors such as saccharin and aspartame, can be advantageously used as flavors other than those described above.

In addition to the above, the food composition of the present invention may include a variety of nutrients, vitamins, minerals (electrolytes), a flavors such as synthetic flavors and natural flavors, coloring agents and thickening agents (cheese, chocolate etc.), pectic acids and salts thereof, alginic acids and salts thereof, organic acids, protective colloid thickening agents, pH adjusting agents, stabilizers, preservatives, glycerin, alcohols, carbonating agents used in carbonated drinks, and the like.

Unless otherwise defined herein, the terms have the meanings commonly used in the art to which the present invention pertains.

Hereinafter, the present invention is described in detail with reference to examples. However, the following examples are illustrative of the present invention and are not intended to limit the scope of the present invention.

Example 1. Analysis of Effect of Bile Acid on the Intranuclear Beta-Catenin Level 1.1 Screening for Discovery of Agonist to Beta-Catenin Experiments were conducted to identify drugs with an enhancement effect on beta-catenin by analyzing the effects of various kinds of bile acid on the intranuclear beta-catenin level. Nuclear beta-catenin luciferase assay was performed to examine effects of treatment with ursodeoxycholic acid, glycochenodeoxycholic acid (GlycochenDCA), taurodeoxycholic acid (TauroDCA), glycocholic acid, taurocholic acid (TauroCA), chenodeoxycholic acid (ChenoDCA), cholic acid, dehydrocholic acid, lithocholic acid and deoxycholic acid (DCA) on the change of the intranuclear beta-catenin level.

Specifically, TCF/LEF reporter_HEK293 cell line (BPS bioscience) was used. The TCF/LEF reporter_HEK293 cell line is a stable cell line in which luciferase is cloned into the TCF/LEF promoter (beta-catenin-binding promoter) in the nucleus. When the level of luciferase is measured after drug treatment, intranuclear beta-catenin levels can be obtained. The TCF/LEF reporter_HEK293 cell lines (BPS Bioscience) were divided into 24 wells ($2\times10^5$ cells) or 96 wells ($2\times10^4$ cells) and cultured until the cells were adhered to the plate bottom. In order to make cells in a resting state, 10% FBS DMEM medium was replaced with 1% FBS medium, and the cells were cultured for one day. The cells were treated with the above-described bile acids in 1 μm or 10 μm and cultured for 24 hours. Thereafter, the activity of luciferase was measured using a luminometer. The measurement results are shown in FIG. 1.

Figure 1:
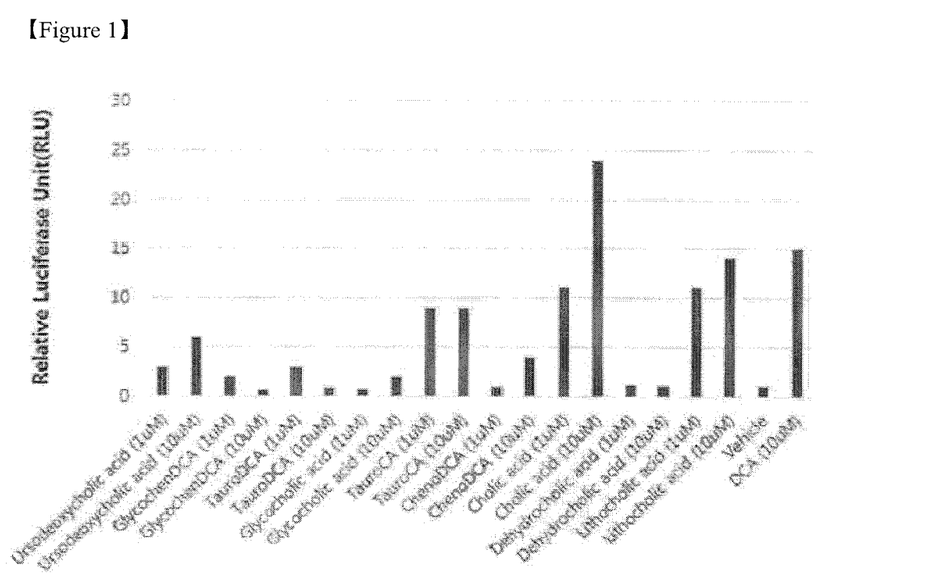
FIG. 1 illustrates the results of a nuclear beta-catenin luciferase assay to determine whether cholic acid, lithocholic acid, and deoxycholic acid increase intranuclear beta-catenin levels.

As shown in FIG. 1, it was confirmed that TauroCA, cholic acid, lithocholic acid, and deoxycholic acid among 10 kinds of bile acids significantly increased beta-catenin levels in the nucleus.

1.2 Identification of the Increase of Intranuclear Transfer of Beta-Catenin by Deoxycholic Acid (DCA)

Western blot was performed to examine the mechanism of intranuclear transfer of beta-catenin by deoxycholic acid (DCA) identified in Example 1.1 above. Cells were treated with 1 μM DCA. After 30 minutes, 1, 2, 4, and 8 hours, western blotting was performed. The results are shown in FIG. 2.

Figure 2:
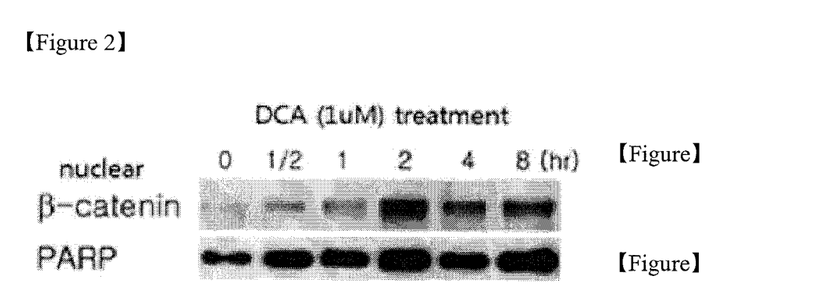
FIG. 2 illustrates the results of western blot analysis of intranuclear transfer of beta-catenin after treatment with deoxycholic acid (DCA).

As shown in FIG. 2, it was observed that intranuclear transfer of beta-catenin was increased from 30 minutes after the treatment with DCA, and the amount of intranuclear beta-catenin of the cells peaked 2 hours later.

Therefore, it was identified that TauroCA, cholic acid, lithocholic acid, and deoxycholic acid increased the level of beta-catenin, which inhibits the opening of mitochondrial permeability transition pore (mPTP), thereby suppressing reperfusion injury. Thus, it has been confirmed that they have potential as candidates for drugs with beta-catenin enhancement effects.

Example 2. Identification of Protective Effect of Bile Acid on Mitochondria-Inhibition of mPTP Opening In order to examine the effect of cholic acid, lithocholic acid, and deoxycholic acid on the mitochondria, which were confirmed to have an effect of increasing the beta-catenin levels in Example 1, TMRM (tetramethylrhodamine, methyl ester, perchlorate) staining method was performed. TMRM is a fluorescent marker that stains normal mitochondria.

Figure 3:
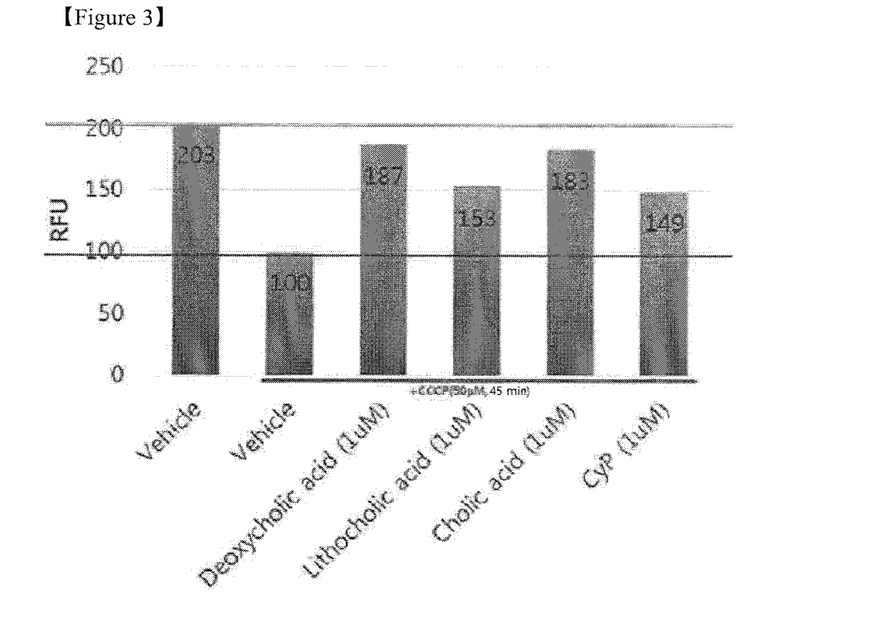
FIG. 3 illustrates the results of TMRM (Tetramethylrhodamine, Methyl Ester, Perchlorate) staining method to determine whether cholic acid, lithocholic acid, and deoxycholic acid have an effect of protecting mitochondria.

Specifically, 293T cells were treated with 1 μM and 10 μM of cholic acid, lithocholic acid, and deoxycholic acid. After 1 hour, the cells were treated with CCCP (chlorophenylhydrazone, 50 μM), which induces similar stimulation to reperfusion into mitochondria to open mPTP and to induce polarization. Thus, mPTP opening and depolarization of mitochondria were induced. After 45 minutes, the cells were washed with PBS, stained with TMRM, and measured using a fluorescent reader. The measurement results are shown in FIG. 3. Cyclosporine A (Cyp), which is a typical inhibitor of mPTP opening, was used as a positive control.

As shown in FIG. 3, Cyp inhibited mitochondrial injury by about 50% in the group treated with Cyp, which was the positive control, and lithocholic acid also inhibited mitochondrial injury to a level similar to that of the positive control group. In particular, it was confirmed that cholic acid and deoxycholic acid had effects of inhibiting mitochondrial injury by about 90%.

Therefore, it was confirmed that the treatment with cholic acid, deoxycholic acid, and lithocholic acid inhibited the opening of mPTP induced and suppressed depolarization of mitochondria, thereby having an excellent effect of protecting mitochondria. Therefore, it was identified that cholic acid, deoxycholic acid and lithocholic acid could inhibit mitochondrial injury by reperfusion to suppress apoptosis or necrosis inducing irreversible tissue and organ injury.

Example 3. Identification of In Vitro Cell Proliferation Effect and Cell Migration Effect of Bile Acid 3.1 Identification of In Vitro Cell Proliferation Effect of Bile Acid Experiments were conducted to examine cell proliferation effects of TauroCA, cholic acid and lithocholic acid among bile acids. Thus, human umbilical vein endothelial cells (HUVECs) were treated with 1 μM TauroCA, cholic acid and lithocholic acid. The cell counting method and CCK-8 staining method were performed to identify cell proliferation effects 24 hours after the treatment with TauroCA, cholic acid and lithocholic acid. The results of these experiments are shown in FIGS. 4A and 4B.

Figure 4:
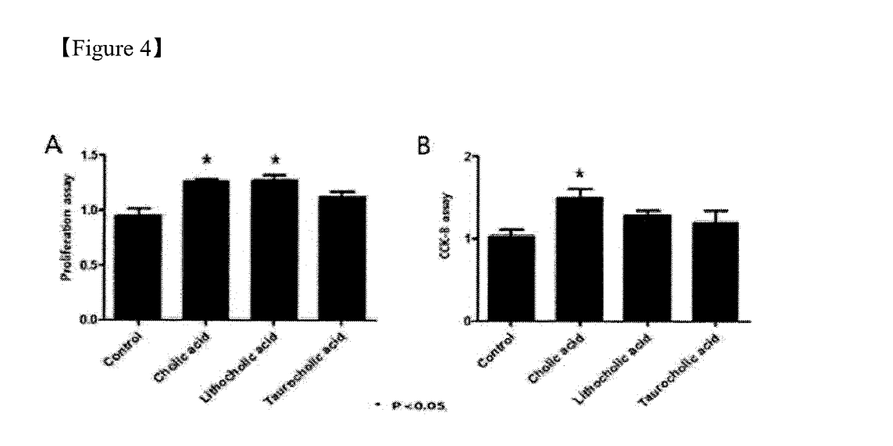
FIG. 4 illustrates the results of cell counting method (FIG. 4A) and CCK-8 staining method (FIG. 4B) to determine cell proliferation effect identified by treating human umbilical vein endothelial cells (HUVECs) with TauroCA, cholic acid and lithocholic acid among bile acids.

As shown in FIG. 4A, the proliferation assay indicated that cholic acid and lithocholic acid had more significant cell proliferation effects than the control group. As shown in FIG. 4B, the CCK-8 assay indicated that cholic acid had significant a cell proliferation effect. Therefore, it was confirmed that cholic acid and lithocholic acid had effects of inhibiting ischemia reperfusion-injury through cell proliferation.

3.2 Identification of In Vitro Cell Migration Effect of Bile Acid

Experiments were conducted to examine cell migration effects of TauroCA, cholic acid and lithocholic acid among bile acids. Thus, human umbilical vein endothelial cells (HUVECs) were treated with 1 μM TauroCA, cholic acid and lithocholic acid. The cells were counted using Boyden chamber to identify cell migration effects of TauroCA, cholic acid and lithocholic acid. The results of these experiments are shown in FIGS. 5A and 5B.

Figure 5:
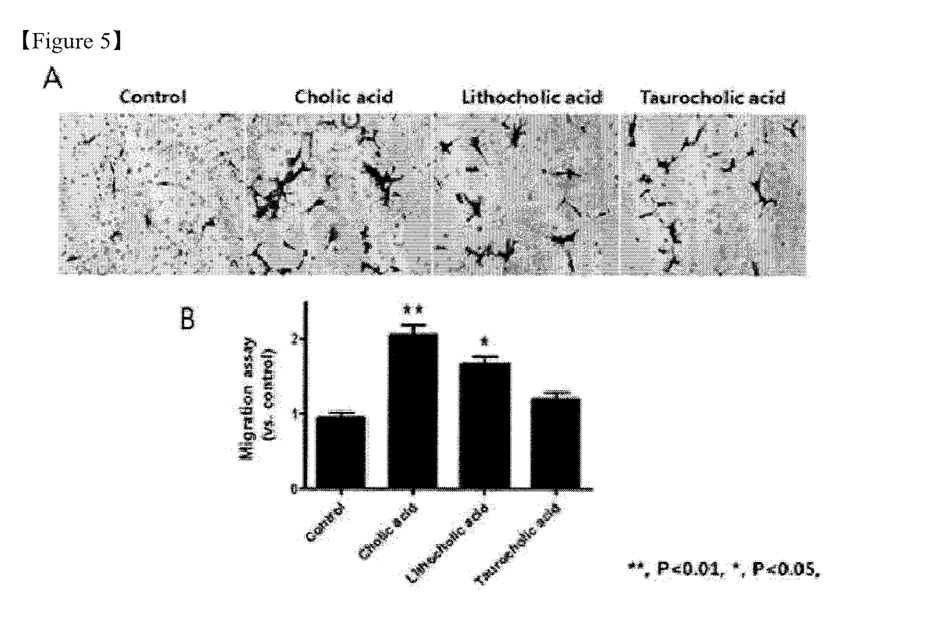
FIG. 5 illustrates the results of cell staining method (FIG. 5A) and cell counting method (FIG. 5B) that counts the number of cells passing through the membrane using Boyden chamber to determine cell migration effect identified by treating human umbilical vein endothelial cells (HUVECs) with TauroCA, cholic acid and lithocholic acid among bile acids.

As shown in FIG. 5A, it was confirmed that their cell migration effects caused by treating with cholic acid, TauroCA, and lithocholic acid were significantly higher than that of the control group. Also, as shown in FIG. 5B, the migration assay confirmed that the cell migration by the treatment with cholic acid and lithocholic acid was significantly increased than that of the control group. In particular, cholic acid showed about 2 times more cell migration than the control group and showed the best migration effect.

Therefore, it was confirmed that cholic acid and lithocholic acid migrated cells and had effects of inhibiting ischemia-reperfusion injury through cell migration.

Figure 6:
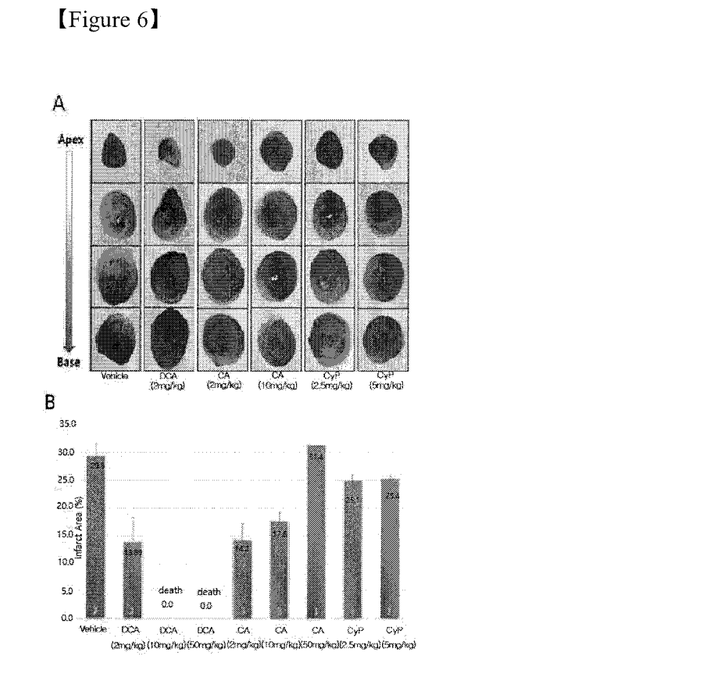
FIG. 6 illustrates a tissue photograph of a mouse model identifying the inhibitory effect of bile acid on mouse reperfusion injury (FIG. 6A) and results of quantifying the area of the infarcted tissue relative to the total area in % in the tissue photograph (FIG. 6B).

Example 4. Preparation of Reperfusion Injury Mouse Model and Identification of Inhibitory Effect of Bile Acid on Mouse Reperfusion Injury In order to prepare a reperfusion injury mouse model, Balb/C mice (8 weeks old) were anesthetized with ketamine. The tube was intubated into the airway and connected to a respirator. The left side of the mouse was then corrected to the upper side, and the skin was incised. The gap was widened between the third and fourth ribs so as to fix the heart to be exposed. The deoxycholic acid or cholic acid, which was the most effective in screening and in vitro assays, was injected into the left ventricle in a concentration of 2 mg/kg, 10 mg/kg and 50 mg/kg using a vascular injection method. Thereafter, the left coronary artery was tied and then loosened 40 minutes later and sutured. After 24 hours, the hearts were harvested and frozen at −20° C. for 4 hours. The hearts were quaternized in 2 mm thickness. Each tissue was cultured and stained with 2% TTC (in PBS) solution for 40 minutes. Then, the tissue was transferred to a 10% formalin solution and stored for one day. Photographs were taken and the results are shown in FIG. 6A. Further, in the tissue photograph, the area of the infarcted tissue relative to the total area was quantified as %, and the result is shown in FIG. 6B. Cyclosporine A (Cyp), a substance that inhibits the opening of mPTP, was used as a positive control.

As shown in FIG. 6A, it was confirmed that living tissue was stained red and infarcted tissue was stained white. It was confirmed that the tissues treated with 2 mg/kg of deoxycholic acid and 2 mg/kg or 10 mg/kg of cholic acid were mostly reddish with almost no white staining compared to the control group.

Further, as shown in FIG. 6B, the positive control group Cyp (5 mg/kg) showed a reduction of the infarcted area by about 20%, whereas the group treated with 2 mg/kg of deoxycholic acid showed a decrease by about 50% and the group treated with 2 mg/kg and 10 mg/kg of cholic acid showed a decrease by about 50% and about 40%, respectively. However, in the group treated with deoxycholic acid, cells died at a concentration of 10 mg/kg or more, and deoxycholic acid showed the effect at a concentration of 2 mg/kg or less. The cholic acid showed the best efficacy at a concentration of 2 mg/kg. Therefore, it was confirmed that the effect of suppressing reperfusion injury is excellent when the concentration is low.

Therefore, it was confirmed that low concentrations of deoxycholic acid and cholic acid could be used as an inhibitor of cardiac injury after reperfusion.

Example 5. Identification of the Inhibitory Effect of Bile Acid on Mouse Myocardial Necrosis in Reperfusion Injury Mouse Model In order to confirm the inhibitory effect of deoxycholic acid among the bile acids on myocardial necrosis caused by reperfusion injury, the test was performed to confirm mouse myocardial necrosis using Annexin-Vivo750 fluorescent dye.

Figure 7:
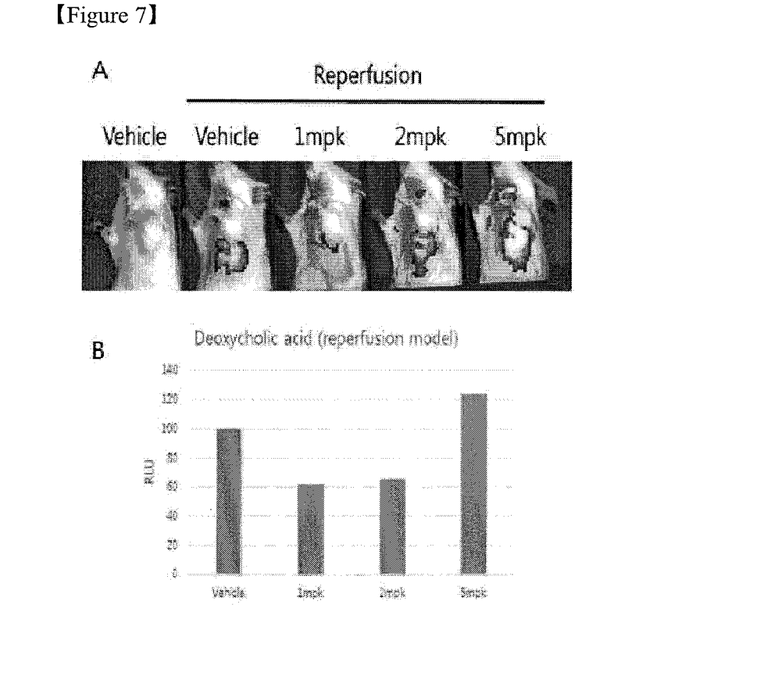
FIG. 7 illustrates graphs showing the results of staining with Annexin-Vivo 750 fluorescence dye (FIG. 7A) and the effect of deoxycholic acid concentration on myocardial cell death reduction in order to examine inhibition of myocardial necrosis by reperfusion injury by deoxycholic acid in bile acid (FIG. 7B).

After 24 hours, Annexin-Vivo750 fluorescent dye was injected into the mouse model prepared in Example 3 to examine the effect of deoxycholic acid (1, 2, 5 mg/kg (mpk)) by the concentration. The results are shown in FIGS. 7A and 7B. Annexin dyes are known to bind where apoptosis occurs and to show fluorescence.

As shown in FIG. 7A, it was confirmed that the heart was not stained in the control group without reperfusion, but the control group with reperfusion surgery showed strong fluorescence. Further, as shown in FIG. 7B, it was confirmed that the group treated with 1 mpk or 2 mpk deoxycholic acid showed the effect of decreasing myocardial death by 40% or more compared to the control group with reperfusion surgery. Therefore, it was confirmed that deoxycholic acid with low concentration could be used as an inhibitor of reperfusion injury due to effective inhibition of ischemia-reperfusion injury.

Although the present invention has been described with the preferred embodiments as described above, it is possible to make various modifications and variations without departing from the spirit and scope of the present invention. The appended claims are intended to cover such modifications and changes as fall within the scope of the present invention.

Formulation Example 1: Preparation of Medicines 1.1 Preparation of Capsules
Bile acid: 100 ml
Corn starch: 100 mg
Lactose: 100 mg
Magnesium stearate: 2 mg
The above components are mixed and filled into gelatin capsules to prepare tablets according to a conventional capsule preparation method.

1.2 Preparation of Injections
Bile acid: 100 ml
Sterile sterilized water for injection: suitable amount
pH adjuster: suitable amount
The above components are included in the above amount per 1 ampoule (2 ml) according to a conventional injection preparation method.

1.3 Preparation of Liquids
Bile acid: 100 ml
Sugar: 20 g
Isomerized glucose: 20 g
Lemon favor: suitable amount
Purified water was added to make the total volume of 1,000 ml. The above components are mixed, then filled in a brown bottle and sterilized to prepare liquids according to a conventional liquid preparation method.

Formulation Example 2: Preparation of Food 2.1 Preparation of Flour Food
0.1 parts by weight to 10.0 parts by weight of the food composition of the present invention was added to wheat flour, and the mixture was used to prepare bread, a cake, a cookie, a cracker and a noodle for a health improving food.

2.2 Preparation of Dairy Products
0.1 part by weight to 1.0 part by weight of the food composition of the present invention was added to milk, and the mixture was used to prepare various dairy products such as butter and ice cream.

The invention claimed is:

1. A method of preventing or treating myocardial ischemia-reperfusion injury, the method comprising: administering a bile acid or pharmaceutically acceptable salt thereof to a subject in need thereof, wherein the bile acid is at least one selected from the group consisting of deoxycholic acid and lithocholic acid.

2. The method of claim 1, wherein the ischemia-reperfusion injury is caused by trauma or reperfusion surgery.

3. The method of claim 1, wherein the bile acid or pharmaceutically acceptable salt thereof is administered to a subject via intraperitoneal administration, intranasal administration, intravenous injection, subcutaneous injection, intracerebrospinal injection, inhalation administration or oral administration.

4. The method of claim 1, wherein the bile acid or pharmaceutically acceptable salt thereof is an inhibitor of mitochondrial permeability transition pore (mPTP) opening.

5. The method of claim 1, wherein the bile acid or pharmaceutically acceptable salt thereof is administered in an amount of 0.1 mg/kg/day to 10 mg/kg/day.

* * * * *